(12) United States Patent
Everett et al.

(10) Patent No.: US 9,101,293 B2
(45) Date of Patent: Aug. 11, 2015

(54) AUTOMATED ANALYSIS OF THE OPTIC NERVE HEAD: MEASUREMENTS, METHODS AND REPRESENTATIONS

(75) Inventors: Matthew J. Everett, Livermore, CA (US); Jonathan D. Oakley, Pleasanton, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 249 days.

(21) Appl. No.: 13/210,129

(22) Filed: Aug. 15, 2011

(65) Prior Publication Data

US 2014/0081130 A1    Mar. 20, 2014

Related U.S. Application Data

(63) Continuation of application No. 12/850,882, filed on Aug. 5, 2010, now abandoned.

(51) Int. Cl.
*A61B 6/00* (2006.01)
*A61B 3/10* (2006.01)
*A61B 3/12* (2006.01)

(52) U.S. Cl.
CPC .............. *A61B 3/102* (2013.01); *A61B 3/1225* (2013.01)

(58) Field of Classification Search
CPC .............................. A61B 3/102; A61B 3/1225
See application file for complete search history.

(56) References Cited

U.S. PATENT DOCUMENTS

| | | | |
|---|---|---|---|
| 6,129,682 A | 10/2000 | Borchert et al. | |
| 6,415,173 B1 | 7/2002 | Sponsel et al. | |
| 6,698,885 B2 | 3/2004 | Berger et al. | |
| 7,203,351 B1 | 4/2007 | Swindale et al. | |
| 7,301,644 B2 | 11/2007 | Knighton et al. | |
| 7,505,142 B2 | 3/2009 | Knighton et al. | |
| 7,659,990 B2 | 2/2010 | Knighton et al. | |
| 7,712,898 B2 | 5/2010 | Abramoff et al. | |
| 7,798,647 B2 * | 9/2010 | Meyer et al. | 351/246 |
| 2006/0187462 A1 * | 8/2006 | Srinivasan et al. | 356/479 |
| 2007/0195269 A1 | 8/2007 | Wei et al. | |
| 2009/0268159 A1 * | 10/2009 | Xu et al. | 351/206 |

OTHER PUBLICATIONS

Yang et al (Physiologic Intereye Differences in Monkey Optic Nerve Head Architecture and Their Relation to Changes in Early Experimental Glaucoma, Investigative Ophthalmology & Visual Science, Jan. 2009, vol. 50, No. 1).*

Chen et al (Spectral Domain Optical Coherence Tomography and Glaucoma, Int Ophthalmol Clin. 2008 ; 48(4): 29-45. doi:10.1097/II.*

(Continued)

*Primary Examiner* — Unsu Jung
*Assistant Examiner* — Serkan Akar
(74) *Attorney, Agent, or Firm* — Morrison & Foerster LLP

(57) ABSTRACT

The present invention relates to structural analysis of the optic nerve head (ONH). In one approach, a 3D volume of intensity data which includes the optic nerve head is acquired using an optical coherence tomography (OCT) system. The vitreoretinal interface (VRI) and the optic disc margin are identified from the 3D data. The minimum area of a surface from the optic disc margin to the VRI is determined. This minimum area can be displayed as an image or in the alternative, a value corresponding to this minimum area can be displayed. The minimum area measurement provides relevant clinical information to determine the health of the eye.

52 Claims, 13 Drawing Sheets

(56) References Cited

OTHER PUBLICATIONS

Anderson, Douglas R., "The Optic Nerve in Glaucoma", Duane's Ophthalmology, vol. 3, Chapter 48, 2004, 37 pages.

Chen, Teresa C., "Spectral Domain Optical Coherence Tomography in Glaucoma: Qualitative and Quantitative Analysis of the Optic Nerve Head and Retinal Nerve Fiber Layer (an AOS thesis)", Transactions of the American Ophthalmological Society, vol. 107, 2009, pp. 254-281.

Choma et al., "Senstivity Advantage of Swept Source and Fourier Domain Optical Coherence Tomography", Optics Express, vol. 11, No. 18, 2003, pp. 2183-2189.

Coleman et al., "Interobserver and Intraobserver Variability in the Detection of Glaucomatous Progression of the Optic Disc", Journal of Glaucoma, vol. 5, No. 6, 1996, pp. 384-389.

Frohman et al., "Optical Coherence Tomography: A Window into the Mechanisms of Multiple Sclerosis", Nature Clinical Practice Neurology, vol. 4, No. 12, 2008, pp. 664-675.

Hu et al., "Automated Segmentation of Neural Canal Opening and Optic Cup in 3D Spectral Optical Coherence Tomography Volumes of the Optic Nerve Head", Investigative Ophthalmology and Visual Science, vol. 51, No. 11, 2010, pp. 5708-5717.

Knighton et al., "Structure of the Optic Nerve Head as Assessed by Spectral-Domain Optical Coherence Tomography", Investigative Ophthalmology and Visual Science, vol. 47, 2006, 2 pages.

Leung et al., "Analysis of Retinal Nerve Fiber Layer and Optic Nerve Head in Glaucoma with Different Reference Plane Offsets, Using Optical Coherence Tomography", Investigative Ophthalmology and Visual Science, vol. 46, No. 3, 2005, pp. 891-899.

Manassakorn et al., "Comparison of Optic Disc Margin Identified by Color Disc Photography and High-Speed Ultrahigh-Resolution Optical Coherence Tomography", Archives of Ophthalmology, vol. 126, No. 1, 2008, 15 pages.

Medeiros et al., "Detection of Glaucoma Progression with Stratus OCT Retinal Nerve Fiber Layer, Optic Nerve Head, and Macular Thickness Measurements", Investigative Ophthalmology and Visual Science, vol. 50, No. 12, 2009, pp. 5741-5748.

Minckler, Don S., "The Organization of Nerve Fiber Bundles in the Primate Optic Nerve Head", Archives of Ophthalmology, vol. 98, 1980, pp. 1630-1636.

Morgan, Je, "Circulation and Axonal Transport in the Optic Nerve", Eye, vol. 18, 2004, pp. 1089-1095.

Poli et al., "Analysis of HRT Images: Comparison of Reference Planes", Investigative Ophthalmology and Visual Science, vol. 49, No. 9, 2008, pp. 3970-3975.

Povazay et al., "Minimum Distance Mapping Using Three-Dimensional Optical Coherence Tomography for Glaucoma Diagnosis", Journal of Biomedical Optics, vol. 12, No. 4, 2007, pp. 041204-1-041204-8.

Radius et al., "The Course of Axons Through the Retina and Optic Nerve Head", Archives of Ophthalmology, vol. 97, 1979, pp. 1154-1158.

Radius, Ronald L., "Thickness of the Retinal Nerve Fiber Layer in Primate Eyes", Archives of Ophthalmology, vol. 98, 1980, pp. 1625-1629.

Tielsch et al., "Intraobserver and Interobserver Agreement in Measurement of Optic Disc Characteristics", Ophthalmology, vol. 95, No. 3, 1988, pp. 350-356.

Xu et al., "Automated Assessment of the Optic Nerve Head on Stereo Disc Photographs", Investigative Ophthalmology and Visual Science, vol. 49, No. 6, 2008, 16 pages.

Xu et al., "Translation Histogram Based Hierarchical Algorithm for 3-D Optic Nerve Head Modeling", Conference Proceeding IEEE Engineering in Medicine and Biology Society, 2007, 8 pages.

Savini et al., "Agreement Between Optical Coherence Tomography and Digital Stereophotography in Vertical Cup-to-Disc Ratio Measurement", Graefe's Archive for Clinical and Experimental Ophthalmology, vol. 247, No. 3, 2009, pp. 377-383.

Heidelberg on-line FAQs 14 and 15, © 2004-2011 Heidelberg Engineering, Inc., Available at: http://www.heidelbergengineering.com/technical-support-heidelberg-engineering/faq-topics/hrt3-glaucoma-faqs/#faq_791.

\* cited by examiner

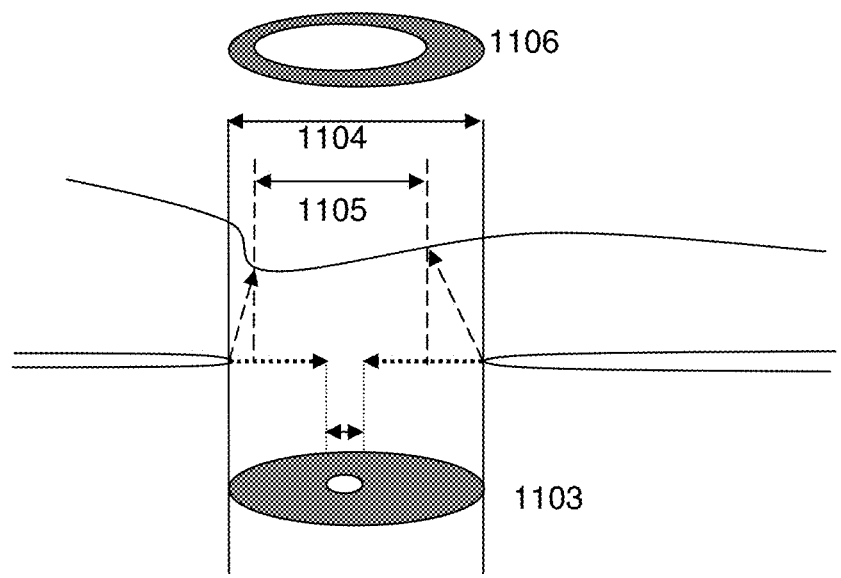
FIG. 11a
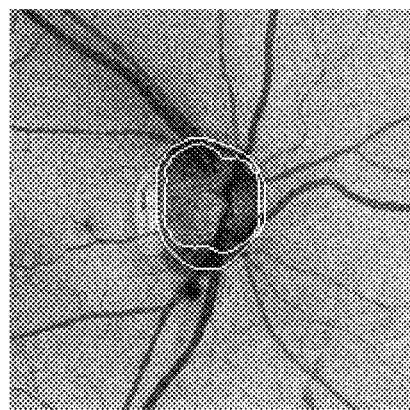 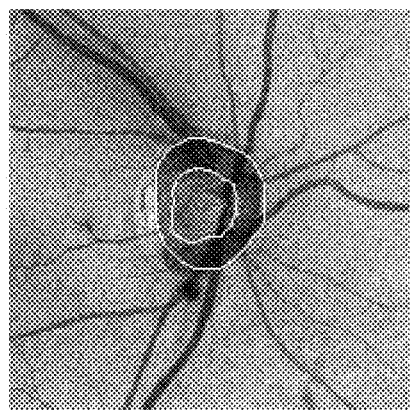
FIG. 11b          FIG. 11c

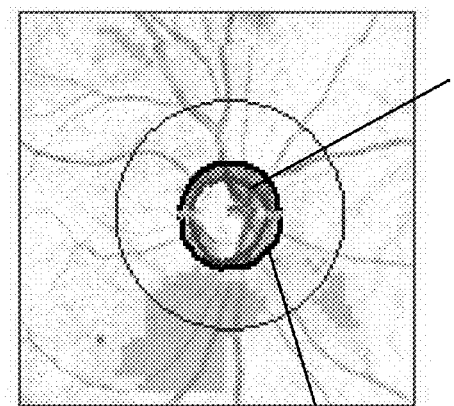
FIG. 13a
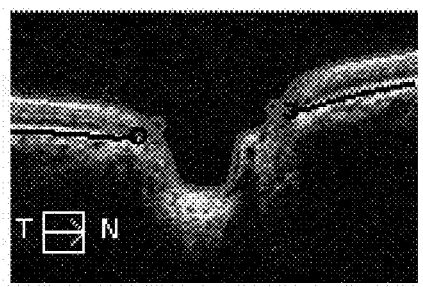
FIG. 13b
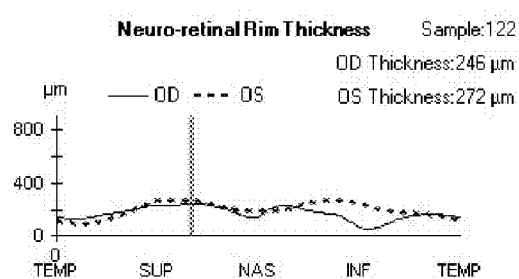
FIG. 13c
|  | OD | OS |
|---|---|---|
| Average RNFL Thickness |  |  |
| RNFL Symmetry |  |  |
| Rim Area | 0.77 mm² | 0.78 mm² |
| Disc Area | 1.94 mm² | 1.59 mm² |
| Average C/D Ratio | 0.76 | 0.70 |
| Vertical C/D Ratio | 0.80 | 0.62 |
| Cup Volume | 0.495 mm³ | 0.306 mm³ |
FIG. 13d

AUTOMATED ANALYSIS OF THE OPTIC NERVE HEAD: MEASUREMENTS, METHODS AND REPRESENTATIONS

PRIORITY

This application is a continuation of U.S. patent application Ser. No. 12/850,882, filed Aug. 5, 2010, the disclosure of which is incorporated herein by reference in its entirety.

TECHNICAL FIELD OF THE INVENTION

One or more embodiments of the present invention relate generally to structural analysis of the optic nerve head (ONH) imaged in three dimensions (3D), the methods of attaining said measurements, and their representations. In particular, this invention provides a fully automated method that provides specific and sensitive measurements that emulate the structural measurements inferred by an expert clinician based on experience, anatomical knowledge, and where stereo images are available, depth cues.

BACKGROUND OF THE INVENTION

The optic nerve is made up of approximately 1 to 1.5 million nerve fibers or axons along with supporting glial cells and blood vessels (Anderson, D. (2004) "The Optic Nerve Head in Glaucoma" Duane's Ophthalmology). The optic nerve head (ONH) is the exit in the outer retina where all the nerve fibers pass through the chorioscleral canal or neural canal opening on their path to the brain. As shown in FIG. 1, the nerve fibers i.e. 102 are shown in the figure as striations distributed across the entire retina in the nerve fiber layer (NFL) or retinal nerve fiber layer (RNFL), and converge at the ONH 101. At this point, the nerve fiber bundles are at their most concentrated, forming what is known as the neuroretinal rim 103. The neuroretinal rim is a 3D structure bounded by the optic disc margin on the outside and the optic cup margin on the inside. The optic cup is a physiological excavation that results if the chorioscleral canal is larger than the optic nerve itself. As will be discussed further below, the boundary of the optic cup margin is open to interpretation and such vagueness has hindered the clinical utility of measurements of the neuroretinal rim.

Different optic neuropathies manifest themselves as atrophying of nerve fibers. In glaucoma, for example, the NFL thins as a direct result of ganglion cell apoptosis (the retinal neurons responsible for transmitting visual information) which leads to nerve fiber loss. In other types of optic neuropathies the NFL will also typically thin as a general result of nerve fiber injury (Frohman E et al. (2008). "Optical Coherence Tomography: A Window into the mechanisms of multiple sclerosis" Nat. Clin. Prac. Neurol. 4(12): 664-675). In theory, any nerve fiber loss will manifest itself as thinning at the neuroretinal rim as any retinal nerve fiber belongs to that particular landmark. Therefore, an objective and accurate structural measurement of the neuroretinal rim is central to disease management and diagnosis. Unique to the eye, the ganglion cell nerve fibers are unmylenated, and the ability to directly measure them creates potential diagnostics in the field of neurology.

The gold-standard structural assessment of the ONH is based on a manual estimation of the delineation of optic disc and optic cup margins performed by an expert clinician based on an ophthalmic examination with anophthalmascope and/ or fundus photography (see for example U.S. Pat. No. 6,415, 173). This assessment is highly subjective. Using stereo fundus photography, depth cues may be inferred to improve the estimate, but the method remains subjective, indirect, and variable (See for example Coleman A. et al. (1996). "Interobserver and intraobserver variability in the detection of glaucomatous progression of the optic disc" J. Glaucoma 5:384-9 and Tielsch J. et al. (1988) "Intraobserver and interobserver agreement in measurement of optic disc characteristics" Ophthalmology 95:350-6). Furthermore, the disc margin is often hard to see in fundus images as a result of either poor image quality or because the boundary is obscured by other anatomy such as the nerve fiber bundles themselves or the vessel structure also converging in that region. The measurements are also difficult to repeat because of their subjective nature hindering their ability to accurately determine if changes in the metric are a result of disease progression or, more simply, the difference in the subjective evaluation. While efforts have been made to develop means to remove subjectivity, by allowing comparison over time, by directly superimposing two digital images (see for example U.S. Pat. No. 6,698,885), and automation to identify pixels associated with cup, rim and vessels (see for example, U.S. Pat. No. 7,712,898), the method remains largely subjective in nature.

Automated measurements of the ONH exist, but have different drawbacks. One commercial device offering such functionality is the HRT (Heidelberg Retina Tomograph, Heidelberg Engineering, Inc, Germany), which uses a 670 nm wavelength laser as its light source to build a 3D image of the surface topography of the ONH (see for example U.S. Pat. No. 7,203,351). It is a confocal system and covers approximately 2500 microns axially. Its ability to accurately image the topography of the ONH relies entirely on the user's choice of the focal plane, about which a series of 2D confocal images are acquired—spaced at around 80 microns apart—and then summed to form a representative 2D image. A 3D image is constructed based on the intensity profile across the axial range; depth is simply the profile's largest response. FIG. 2 shows a portion of the analysis report of the HRT. The image shows three regions corresponding to the optic cup and optic disc analysis. The central region 201 corresponds to the optic cup and the other two regions 202 and 203 correspond to the optic disc where 202 indicates the slope.

The HRT's ability to automatically measure ONH structure relies on a manual delineation of the optic disc margin, and then bases the optic cup margin as the intersection of the vitreoretinal interface (VRI) or inner limiting membrane (ILM) at a fixed offset from the disc's reference plane, which is automatically defined. As such, the HRT simply determines the optic cup margin as an area away from the reference plane and within the contour of the optic disc margin. This is not based on a given repeatable landmark, as might be used by the clinician, and the variability of the reference plane itself is an additional source of variation in the measurement (See Heidelberg on-line FAQ: http://www.heidelbergengineering-.com/technical-support-heidelberg-engineering/faq-topics/ hrt3-glaucoma-faqs/#faq_791 and Poli A. et al. (2008). "Analysis of HRT images: comparison of reference planes" Ophthalmology & Visual Science 49(9)).

The Stratus-OCT (Carl Zeiss Meditec, Inc, Dublin Calif.) with an axial resolution of approximately 10 microns, is able to find the disc margin automatically, but due to a similar definition of the optic cup margin as the HRT in terms of an offset, still suffers from robustness issues. FIG. 3 displays a two-dimensional (2D) illustration of how the optic cup margin is defined in the Stratus system. After defining the optic disc margin 303 at the endpoints of the RPE 302, the optic cup margin 305 is defined in reference to a plane parallel to the plane of the optic disc 303 at an offset 304 where it intersects the VRI 301. The choice of the offset from the plane of the disc is arbitrary and determines the size of the cup, leaving its anatomical meaning unclear. Should the user wish to best correlate the cup as then delineated by the automated software to that defined by the clinician from fundus photographs, it needs to be manually adjusted (see Savini G et al. (2009). "Agreement between optical coherence tomography and digital stereophotography in vertical cup-to-disc ratio measurement" *Graefe's Arch. Clin. Exp. Ophthalmol* 247(3):377-383). More importantly, the choice of offset can inadvertently affect the ability of the measurement to distinguish disease from normal structure (see Leung C. et al (2005). "Analysis of Retinal nerve fiber layer and optic nerve head in glaucoma with different reference plane offsets using optical coherence tomography" *Invest Ophthalmol and Vis Sci* 46:891-899).

This definition of the cup in terms of an offset has continued with some newer Spectral Domain OCT (SD-OCT) devices. FIG. 4 shows a cross-sectional schematic illustrating the definition of cup and disc as available in the commercial software (version 4.0) of the RTVue instrument (Optovue Inc., Fremont, Calif.). The optic disc 401 is defined as the termination of the RPE 402. This defines the disc's plane. The optic cup 403 is defined to be where a plane at an offset of 150 microns above that plane (a line in the 2d cross section above) intersects the VRI 404. Based on these definitions, measurements relating to the neuroretinal rim including the rim volume (shown in cross-sectional view) 405 and the nerve head volume (shown in cross-sectional view) 406 are derived.

In light of the above there is a need for an automated, repeatable and accurate method of analyzing the ONH that provides anatomically relevant and unambiguous definitions of the optic disc and optic cup margins to make and display clinically meaningful measurements.

SUMMARY

One or more embodiments of the present invention satisfy one or more of the above-identified needs in the prior art. In particular, one embodiment of the present invention is a method for performing analysis on the optic nerve head of a patient comprising the steps of acquiring a 3D image data set, defining an optic disc margin, determining a surface between the optic disc margin and the vitreoretinal interface (VRI) having the minimum or smallest possible area, and providing an output based on the minimum area surface as a diagnostic of ocular health. In this invention, this minimum surface area is used to define the neuroretinal rim area and with the optic disc, used to define the optic cup margin. This method can be automated and carried out on 3D OCT data.

One means to achieve the identification of the minimum area surface includes dividing the optic disc margin into sectors and for each sector identifying a surface between the optic disc margin and the VRI that has the minimum or smallest area. These areas are then summed to provide an output of rim area based on the total area.

A further and preferred means to determine the minimum area surface includes defining a series of nerve fiber cross-section vectors extending from points around the optic disc margin to the viteroretinal interface (VRI), and calculating effective cross-sectional areas for each of the nerve fiber cross-section vectors. Further aspects of this embodiment include identifying the set of nerve cross section vectors that produce the minimum effective cross-sectional areas at each point around the optic disc margin, calculating the minimum effective cross-sectional areas for each of the points around the optic disc margin, and calculating a total neuroretinal rim cross-sectional area by summing the minimum cross-sectional areas around the optic disc margin.

Improvements to the analysis can be made by applying exclusion criteria to the set of nerve cross section vectors, interpolating between the endpoints of the vectors on the VRI surface, and defining the optic disc margin using interpolation.

Another aspect of the invention is to provide more anatomically meaningful definitions of features of the optic nerve head that allow for unambiguous and repeatable measurements from 3D imaging data. This includes defining the optic disc margin in reference to the endpoints of Bruch's membrane, defining the optic cup margin in the plane of the optic disc margin as the shape whose area is based on the difference in the area of the optic disc and the minimum area surface, and defining the neuroretinal rim thickness as the thickness the nerve fiber layer would be at the intersection with the optic disc surface.

An additional aspect of the invention is to display meaningful representations of the analysis. It is desirable to have a 2D representation that preserves the rim area calculated in 3D. For the sector case, this is accomplished by rotating each sector surface down into the plane of the optic disc margin and adjusting the length of the sector to have the same surface area as the original sector. Similarly this can be accomplished in the vector case by rotating the vectors into the plane of the optic disc margin for each point around the optic disc margin, while adjusting their lengths to maintain the minimum cross sectional area. As the rotated vectors are all in the plane of the optic disc, the rim can be visualized in 2D by viewing the optic disc plane with the inner boundary of the rim being the endpoints of the rotated vectors, and the outer boundary being the optic disc margin. For the case where the optic disc plane is tilted relative to the axis along which the OCT data was collected, these shapes can be displayed from the view that the clinician would see if they were looking along the axis of the ONH (perpendicular to the optic disc) or they can be displayed as if viewed along the axis in which the data was collected. In the second case, the image will be foreshortened due to the viewing angle by cos(theta), where theta is the angle (tilt) between the optic disc plane and OCT data collection axis. One could also view the shapes from an arbitrary angle theta relative to the ONH axis, once again foreshortening the view by cos(theta).

The analysis and resulting representations can be used to diagnose and track the progress of disease states affecting the optic nerve head including various optic neuropathies particularly glaucoma, but also neurological conditions such as multiple sclerosis. Values calculated from the analysis including the nerve fiber area, 3D cup volume, neuroretinal rim thickness and cup to disc ratio can be tracked over time and compared to values in normative databases.

These and other embodiments of the invention will be discussed below with reference to the following figures. It is to be understood that both the foregoing general description and the following detailed description are exemplary and explanatory only and are not restrictive of the invention, as claimed.

BRIEF DESCRIPTION OF THE DRAWINGS

FIG. 7a shows an en face view of a 3D OCT volume. FIG. 7b is a single B-scan from the 3D OCT data set corresponding to the straight line indicated in the en face image. FIG. 7c shows a zoomed in view of the circled region in FIG. 7b.

FIG. 11a illustrates how the representation method preserves the area calculation and differs from a simple projection into 2D. FIG. 11b shows the direct projection of the measurement on the en face image FIG. 11C shows the invented representation displayed on an en face image of the OCT data preserving the depth information from the measurement.

FIGS. 13a-d show different aspects of the analysis output of the invented method.

DETAILED DESCRIPTION

Figure 1:
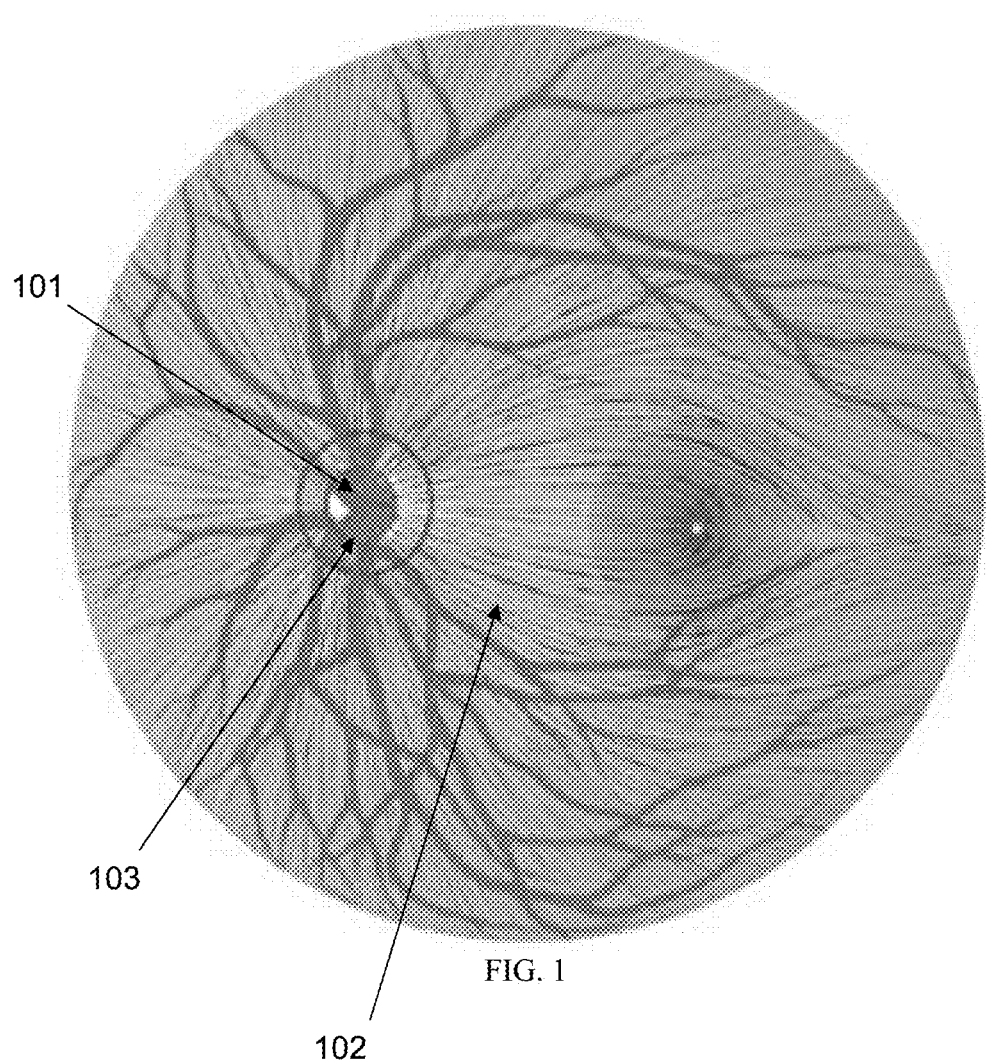
FIG. 1 shows the distribution of the nerve fiber layer in the retina. As the fibers converge to the optic nerve, they bundle up and have the maximum density as they turn and pass through the optic nerve.
Figure 2:
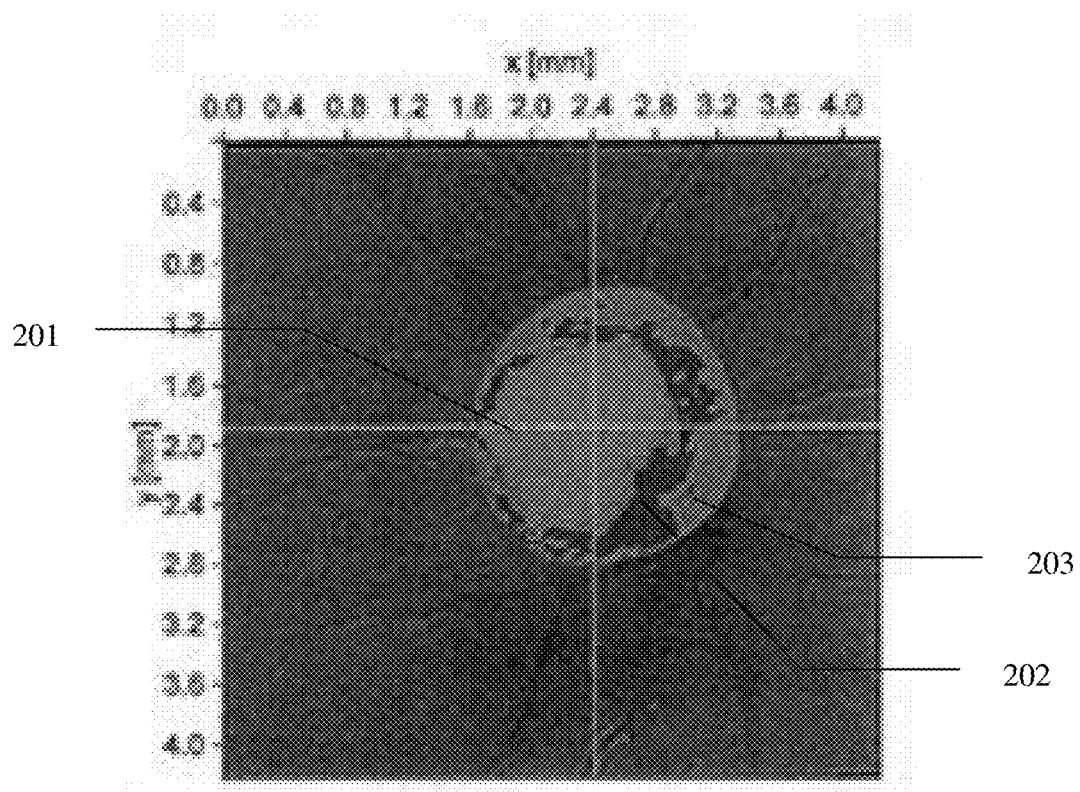
FIG. 2 shows an images of the ONH and corresponding analysis taken with a prior art instrument.
Figure 3:
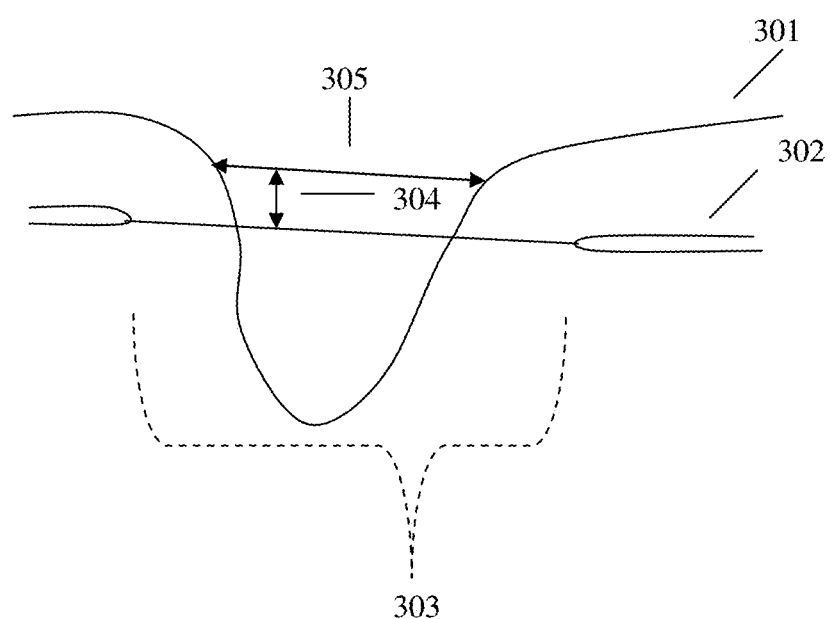
FIG. 3 shows how the assignee's Stratus OCT defines the optic cup margin in terms of an offset from the plane containing the optic disc.
Figure 4:
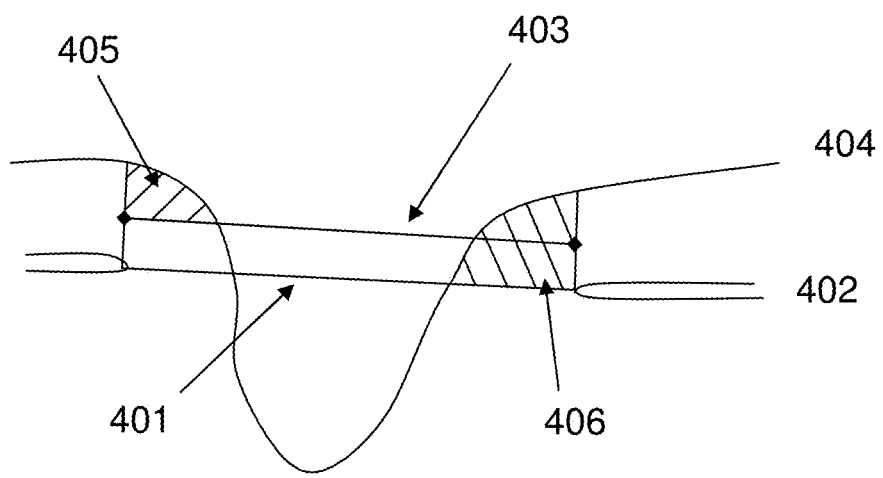
FIG. 4 shows how another prior art device defines the optic cup margin in terms of an offset from the plane containing the optic disc and the related ONH characteristics determined by this definition.

Embodiments of the current invention can be used to perform analysis of the Optic Nerve Head (ONH), particularly the neuroretinal rim, of a patient using 3D imaging data containing tomographic image data. As discussed above, since nerve fiber loss will manifest itself as thinning at the neuroretinal rim as any retinal nerve fiber belongs to that particular landmark, an objective and accurate structural measurement of the neuroretinal rim is central to disease management and diagnosis. By measuring the nerve fibers at the neuroretinal rim, all the nerve fibers that exit the eye are sampled. One can think of an analogy of many ropes coming together, radially, to pass through a single hole. The further away from the optic nerve head, the less concentrated the nerve fibers are (see FIG. 1). As the ropes, or fibers, converge, they can no longer lie in the same plane and must bundle up and over each other. In measurements of the neuroretinal rim, it would be ideal to simply count the number of axons exiting the eye, and to do so repeatedly over time. It would then be possible to accurately stage the disease and very accurately monitor the effect of treatment.

Several things, however, hinder such a direct measurement using current commercial systems. Fundamentally, the fidelity of today's clinically viable imaging systems is such that it is not possible to differentiate structure at the resolution that this would require. In addition to that, the nerve fibers are incased in support material such as blood vessels and glial cells, making it even harder to even assume an overall "count" based on total thickness, a larger scale measurement that can be made. Nonetheless, one can assume a general homogeneity in the overall distribution of such support structures, making total thickness an excellent proxy for axon count. The following describes a new and non-obvious method to measure parameters at the ONH that relate to anatomy that will change as a result of various optic neuropathies including glaucoma. Given the circular nature of the ONH's disc margin, the preferred embodiment to doing this algorithmically is to make cross-section measurements radially about the center of the ONH. Details of the method are described in further detail below.

The fundamental embodiment of the invention involves acquiring a 3D data set containing tomographic image data of the optic nerve head of the patient, defining an optic disc margin that is roughly circular in shape, determining a surface between the optic disc margin and the vitreoretinal interface having the smallest possible area and providing an output based on the minimum area surface as a diagnostic of ocular health. The various steps and alternative embodiments will be discussed in detail below. An important aspect of the subject invention is the determination of a minimum area surface between the optic disc margin and the vitreoretinal interface. This provides an unambiguous, repeatable and clinically meaningful definition of the neuroretinal rim derived by identifying the minimum area of nerve fiber exiting the eye through the choriosceral canal and using this to determine the neuroretinal rim.

Previous approaches have been based on a minimum cross-section distance (or thickness) and are well described (see Povazay B. et al. (2007). "Minimum distance mapping using three-dimensional optical coherence tomography for glaucoma diagnosis" *J. Biomed. Opt.* 12:041204), and have also been commercialized as in the Stratus-OCT (Carl Zeiss Meditec, Inc, Dublin Calif.), albeit with a very sparse cross-sectional sampling around the ONH given the inherently slow acquisition rate of this early generation OCT device. The distinction between minimizing the area and minimizing the distance (or thickness) is important: in defining the boundary based on a minimum area metric, one captures exactly the structure of clinical relevance. The area of the neuroretinal rim relates directly to the number of nerve fibers exiting the eye, the very structures that atrophy and die as a result of various neuropathies. So if the ground truth state of disease is considered to be the number of nerve fibers exiting the eye, it is at their minimum area where the estimate will be most accurate. This all assumes that the course of the axons is to directly exit the eye and not pass through the optic nerve in some sort of spiral pattern. This is a valid assumption, however, both from histological studies (Radius R. et al. (1979). "The course of axons through the retina and optic nerve head" *Arch Ophthalmol* 97 (6):1154-8) and also from descriptions of the axonal course seen in various imaging techniques (Morgan J. (2004) "Circulation and axonal transport in the optic nerve" *Eye* 18:1089-1095).

After obtaining the unambiguous and repeatable characterization of the ONH described above, a further aspect of the invention is to provide a display means or representation that is consistent with the subjective delineation emulating the presentation that would be seen as a result of an ophthalmic examination, the aforementioned structural gold-standard. A representation method that accurately conveys the neuroretinal rim area measurement made in 3D into 2D is described below. This approach preserves the same area in the 2D image as was measured on the surface of the neuroretinal rim and provides a 2D representation of what would be seen if looking along the axis of the ONH. The 2D representation can be transferred back to the 3D volume for display purposes if desired. It can also be displayed as if viewed along the axis of OCT data collection. In this case, the image will be compressed by cos(theta), where theta is the angle (tilt) between the optic disc plane and OCT data collection axis Various means to determine the minimum area surface between the optic disc margin and the vitreoretinal interface can be implemented in an automated fashion. One possible means is to break the optic disc margin into sectors. For each sector, it is possible to identify a surface extending from the optic disc margin to the vitreoretinal interface that has the smallest possible area. These individual minimum areas can be added together to define a surface from which an output can be generated to be used as a diagnostic of ocular health. The analysis is based on the assumption that the nerve fibers run radially to $1^{st}$ order and therefore the calculated area with the sector approach will be slightly different than a calculation based on minimizing the overall area as a whole.

Figure 5:
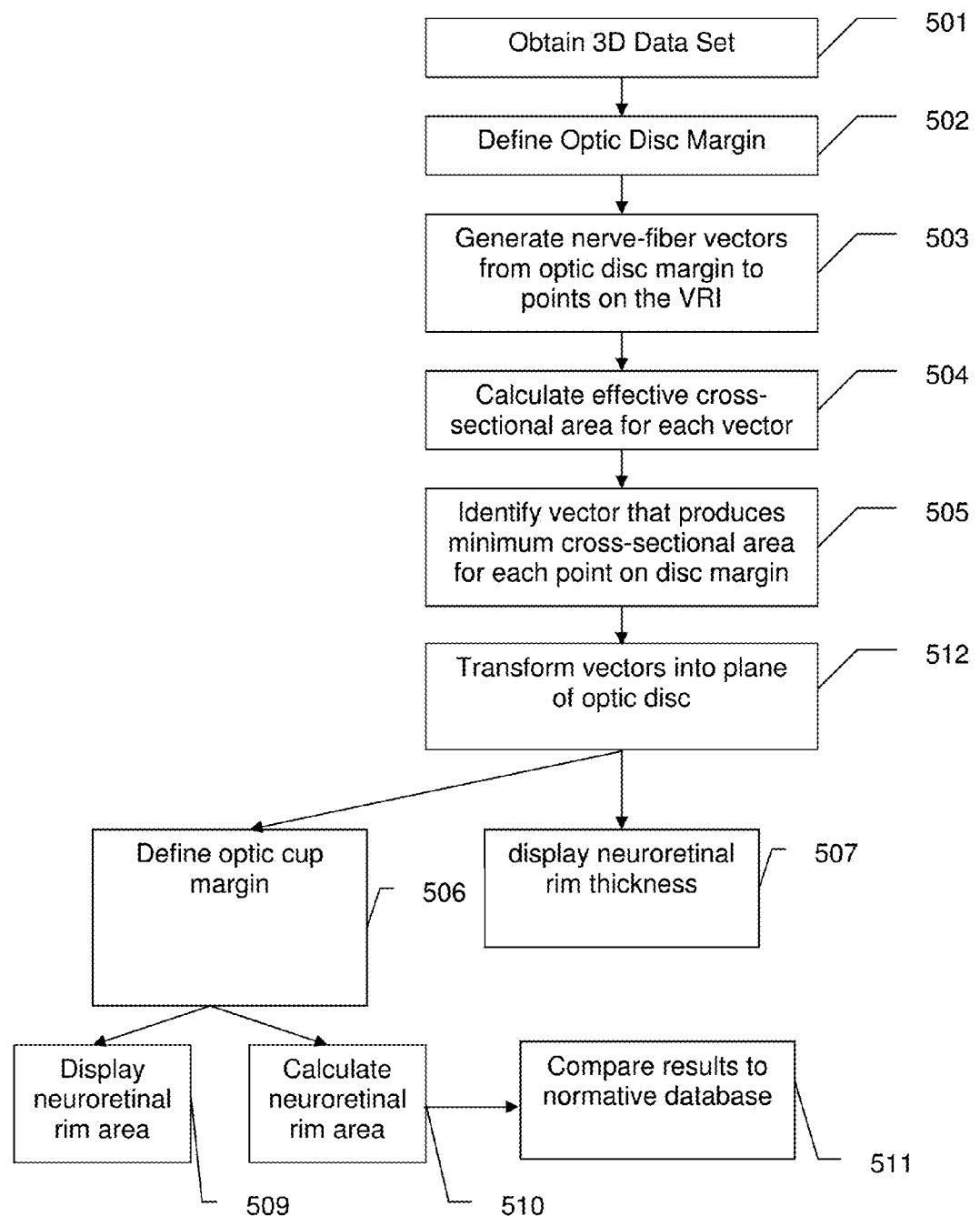
FIG. 5 shows a flow diagram of the steps of various embodiments of the invented ONH analysis method.

The preferred means to implement the determination of the minimum area surface uses a vector based approach. Details of this embodiment are described in detail below. Aspects of this embodiment also apply to the general cases discussed above. FIG. 5 shows a flow chart describing multiple aspects of the preferred embodiment. The overall method involves obtaining a 3D data set (501), defining an optic disc margin (502), generating nerve-fiber vectors from the optic disc margin to points on the VRI (503), calculating effective cross-sectional areas for each vector (504), identifying the vector that produces the minimum effective cross-sectional area for each point on the disc margin (505), and transforming these vectors into the plane of the optic disc while adjusting their lengths to maintain the minimum effective cross-sectional area (512). Upon obtaining this set of transformed minimum cross section vectors, it is possible to define the optic cup margin (506) as the endpoints of these transformed vectors and display (509) and/or calculate (510) the neuroretinal rim area. The calculated neuroretinal rim area can be compared to a normative database (511). The transformed vectors can also be used to display the neuroretinal rim thickness (507). Details for the various steps of the invented method are described in greater detail below.

The first aspect of the invented method outlined in FIG. 5 is to obtain 3D image data from a sample 501. The illustrations included here are based on image data derived from an optical coherence tomography (OCT) system but other 3D imaging modalities could also be utilized. OCT is a non-invasive, in-vivo imaging technique that is based on the back-scatter or reflectivity of light in a medium. The application of interest here is ophthalmic examinations, where the beam of light produced by the OCT device scans the eye through the pupil and the image formation process records the back-scattering profile of the light at each location. The amount of scatter is indicative of the reflectivity of the tissue encountered, and a grayscale cross-sectional image is formed as the light beam sweeps across the field of view (FOV). OCT imaging has dramatically advanced ophthalmic diagnostic capabilities and led also to better understanding of ocular anatomy. It is an established basis of routine ophthalmic practice.

Figure 6:
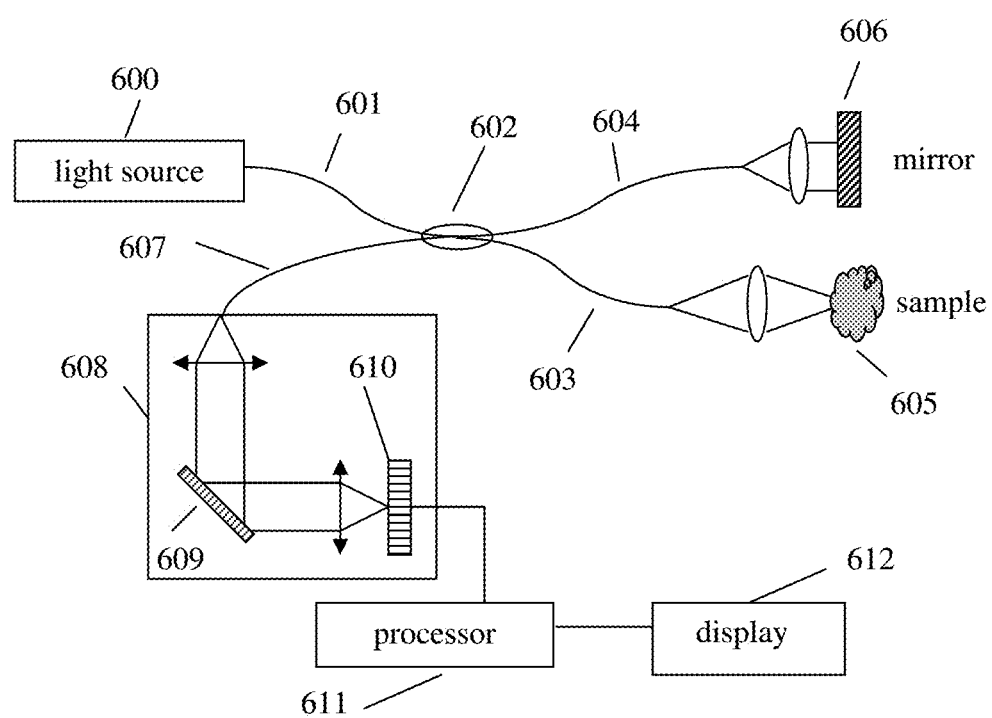
FIG. 6 is a schematic diagram of a basic OCT system capable of generating 3D image data that can be used in the method of the subject invention.

Several implementations of OCT have been developed including time domain (TD-OCT) and frequency domain (spectral domain (SD-OCT) and swept-source (SS-OCT)). FIG. 6 shows a basic block diagram for a spectrometer based SD-OCT system. The light source 600 provides broad bandwidth light to a short length of an optical fiber 601 to an input port of a fiber optic coupler 602, which splits the incoming light beam into the two arms of an interferometer. The two arms each have a section of optical fiber 603 and 604 that guides the split light beam from the fiber coupler 602 to a sample 605 and a reference reflector 606 respectively. For both the sample arm and the reference arm, at the terminating portion of each fiber, there may be a module containing optical elements to collimate or focus or scan the beam. The returned light waves from the sample 605 and the reference reflector 606 are directed back through the same optical path of the sample and reference arms and are combined in fiber coupler 602. A portion of the combined light beam is directed through a section of optical fiber 607 from the fiber coupler 602 to a spectrometer 608. Inside the spectrometer, the light beam is dispersed by a grating 609 and focused onto a detector array 610. The collected data is sent to a processor 611 and the resulting processed data can be displayed on a display 612 or stored in memory for future reference. Note that the principle of operation of a tunable laser based swept source OCT is very similar to that of a spectrometer based spectral domain OCT system (see for example, Choma, M. A. et al. (2003). "Sensitivity advantage of swept source and Fourier domain optical coherence tomography." *Optics Express* 11 (18): 2183-2189), hence the spectral domain OCT system for obtaining the 3D image data set can also be a swept source OCT system.

This example case will be based on the use of SD-OCT; in particular, based on a cube of 200-by-200-by-1024 voxels, that corresponds to a volume of 6 mm-by-6 mm-by-2 mm in the retina. The method could also be applied to other OCT modalities and volumes of tissue. The axial direction here is along the path of the beam of light that enters the eye; the depth resolution covers 2 mm. SD-OCT has a very fast acquisition rate, enabling true volumetric images to be collected in a very short time, maximizing routine clinical utility. For example, a volume of 200-by-200-by-1024 pixels covering a field-of-view (FOV) of 6-by-6-by-2 mm in the eye can be collected in ~1.6 seconds using commercially available instruments. Applying image processing algorithms to such data allows for automatic measurements of structure in the image, where the target measurements pertain, typically, to disease staging.

It is assumed that the obtained 3D image data has been segmented such that the location of the inner limiting membrane (ILM), vitreoretinal interface (VRI), the Retinal Pigment Epithelial layers (RPE) and Bruch's Membrane are known. Many such segmentation algorithms exist and are in commercial products, including the Cirrus HD-OCT™ (Carl Zeiss Meditec Inc., Dublin Calif.). A 2D en face image (or "slab image") is created by integrating voxel information along the Z-axis over a given number of pixels. (see, for example, U.S. Pat. Nos. 7,301,644, 7,505,142, and 7,659, 990) This might be all 1024 pixels, or, alternatively, one can restrict the interpolation range to a meaningful landmark. An example would be to only integrate close to the RPE layer as the resultant 2D image would show more apparent structure from blood vessels or indeed the optic disc.

Figure 7A:
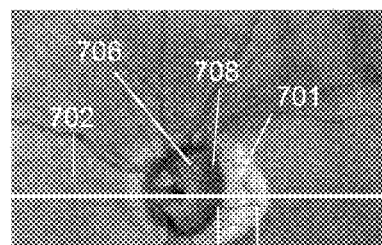
FIGS. 7a, 7b, and 7c illustrate the retraction of the RPE that results from atrophy.
Figure 7C:
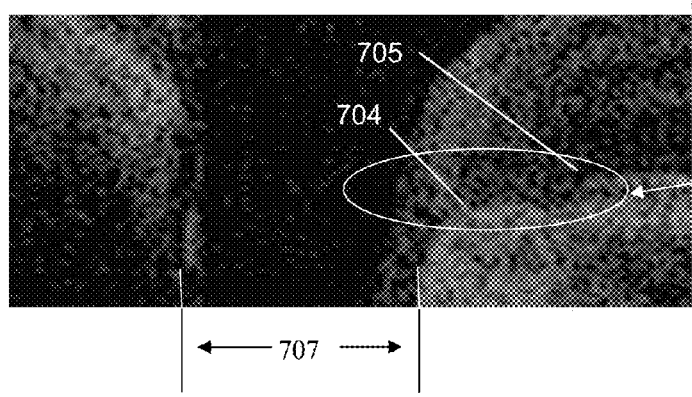
Figure 7B:
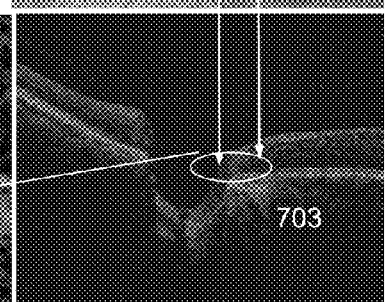

The second aspect of the invented method as described in FIG. 5 is to define the optic disc margin 502. The disc margin is commonly said to be at the end of the RPE/Bruch's membrane complex, or more simply at the end of the RPE which is easiest to identify automatically in OCT data. (see for example Chen T. (2009) "Spectral domain optical coherence tomography in glaucoma: Qualitative and quantitative analysis of the optic nerve head and retinal nerve fiber layer (an AOS thesis)" *Trans Am Ophthalmol Soc* 107:254-281) One drawback in defining the disc margin relative to the RPE is that, in cases of peripapillary atrophy, the end of the RPE can be retracted away from the opening itself. FIG. 7 illustrates this phenomenon. FIG. 7a shows an en face view (6 mm-by-6 mm) of a 3D OCT volume (6 mm-by-6 mm-by-2 mm). The optic nerve head (ONH) or optic disc 706 is the circular region located in the center of the image. The neuroretinal rim 708 is shown as the dark region at the outer edge of the ONH. Atrophy 701 is indicated in the en-face view. Line 702 illustrates the location of the complete B-scan shown in FIG. 7b. FIG. 7c shows an enlargement of the circled region 703 in FIG. 7b. The end of the RPE 705 is clearly visible. Optic disc size would be over estimated if the end of the RPE were chosen to define the disc margin. This is a known issue, but given that the RPE is typically the more obvious landmark, algorithms have tended to use this, and, indeed, suffer accordingly (see Knighton R. et al (2006) "The Structure of the optic nerve head as assessed by spectral domain optical coherence tomography" ARVO poster presentation and Medeiros F. et al (2009). "Detection of glaucoma progression with Stratus OCT retinal nerve fiber layer, optic nerve head, and macular thickness measurements" *Investigative Ophthalmology and Visual Science* 50:5741-5748).

The preferred implementation of the invention described here uses an algorithm that uses the structure supporting the RPE, i.e. Bruch's membrane 704, to define the optic disc margin. This support structure terminates at the edges of the opening of the neuroretinal canal 707. The neuroretinal canal represents the narrowest opening at the back of the eye which is the true exit of the optic nerve fibers and provides a stable landmark for measuring the neuroretinal rim as will be described in further detail below. In a cross-sectional view of the ONH from an OCT data set, Bruch's membrane appears as a thin layer that terminates on either side of the ONH as shown in FIG. 7. The bright layers under Bruch's membrane are the choroid and sclera. The endpoint of Bruch's membrane 704 identifies the outer boundary of the optic disc margin in any cross-section meridian of the 3D image data. This boundary is roughly circular in shape. The optic disc margin can thus be defined by an automatic algorithm identifying the endpoints of the RPE support structure (Bruch's membrane) as landmarks in the 3D image data. There are factors that can hinder the determination of the endpoints of Bruch's membrane; the obvious one intrinsic to all imaging modalities, being noise in the data. A structural hindrance results from vascular anatomy due to vessels converging and exiting at the disc, thereby obscuring the ability to view the membrane. A further aspect of the invention provides means for accounting for these hindrances. Segmenting the vessels and then interpolating the disc delineation across them is one way to accomplish this. Additional means could include filtering or smoothing the input data prior to disc margin identification.

Figure 8A:
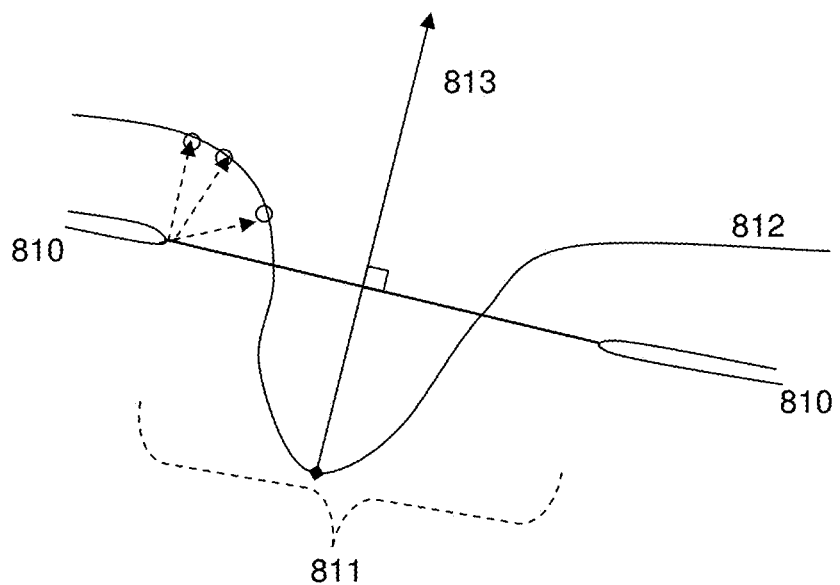
FIG. 8a shows a set of nerve fiber cross section vectors drawn for a particular point on the optic disc margin.

The third aspect of the preferred embodiment of the invented method illustrated in FIG. 5 involves defining a series of nerve fiber cross-section vectors extending from a point around the optic disc margin to the VRI 503. Series of vectors are defined at each of a set of points around the optic disc margin. These vectors point towards a central vector that runs roughly through the center of the optic disc margin and is roughly perpendicular to its surface. FIG. 8a shows how the method would define a series of nerve cross section for a single OCT cross-section. The endpoints of Bruch's membrane 810 define an optic disc margin 811 and a series of vectors can be drawn to the VRI surface 812 from a particular point around the optic disc margin pointing toward the central vector 813 drawn roughly perpendicular to the optic disc margin. The number of vectors drawn to the VRI at a specific point is arbitrary and will determine the level of accuracy of the measurement. The preferred embodiment implements a series of vectors being drawn starting from a 90 degree angle relative to the optic disc margin (parallel to the central vector 813) and proceeding toward zero angle (perpendicular to the central vector). As will be described in further detail below, interpolation between the endpoints of the vectors on the VRI surface is a further aspect of the invention to improve accuracy in the analysis. Similarly, the number of points sampled around the optic disc margin is variable, the figures included show a sparse sampling for illustration purposes, but the preferred embodiment would sample at roughly one degree increments leading to several hundred locations around the optic disc margin.

Figure 8B:
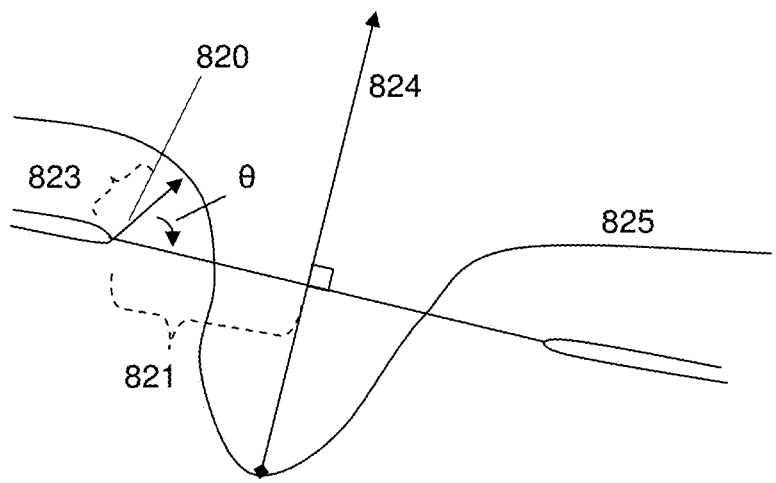
FIG. 8b illustrates the scalar values corresponding to one such nerve fiber vector.

FIG. 8b shows how each nerve fiber cross-section vector 820 can be described by a set of scalar values including, the distance 821 from the central vector 824 to the point on the disc margin in the plane of the optic disc, the angle θ, between the nerve fiber cross section vector 820 and the plane of the optic disc and the distance 823 from the optic disc margin to the VRI 825 along the nerve fiber cross section vector 820. An additional scalar value is provided by the azimuthal angle around the optic disc margin. The azimuthal angle and the distance from the central vector combine to define the origin of the nerve fiber cross section vector, the azimuthal angle and the angle between the nerve fiber cross section vector and plane of the disc combine to define the direction of the vector, and the distance from the disc margin to the VRI defines the length of the nerve fiber cross section vector.

A fourth aspect of the preferred embodiment of the invented method illustrated in FIG. 5 is to calculate effective-cross sectional areas for each of the defined nerve-cross section vectors 504. These cross-sectional areas are a function of at least the distance 821 from the central vector to the point on the disc margin in the plane of the optic disc, the angle θ between the VRI and the plane of the optic disc, and the length 823 of the nerve fiber cross-section vector. While it is possible to have multiple vectors with the same distance to the VRI, associating each vector with an angle relative to the plane of the optic disc margin insures that each vector with the same distance will have a unique area. This provides for a repeatable and clinically meaningful measurement.

Figure 9:
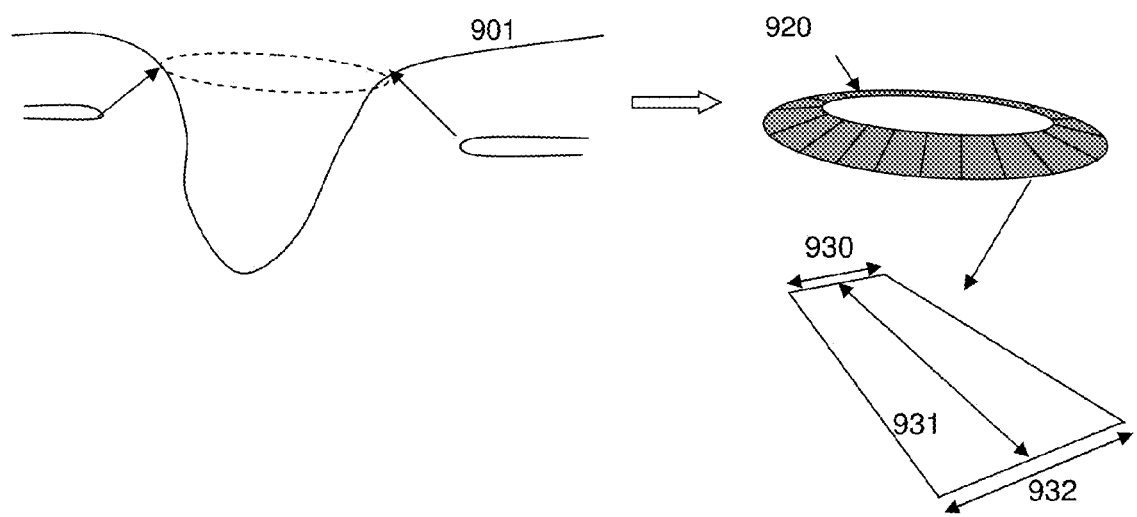
FIG. 9 illustrates how the nerve fiber cross section vectors at points around the optic disc margin in 2D lead to a 3D volume that can be broken down into a set of trapezoids for a given number of points sampled around the neuroretinal rim.

One possible method to calculate the effective cross-sectional areas is to consider each vector as defining a trapezoidal area between a segment on the optic disc margin and a segment on the VRI defined by each vector and the sampling density of points around the optic disc margin. A visualization of this is shown in FIG. 9. The top left shows a 2D representation of the nerve cross section vectors for a specific cross section or meridian of the 3D image data including the VRI 901. The top right shows how this can be extended to a 3D visualization of the neuroretinal rim 920 for a vector from each of a series of points around the optic disc margin and the bottom shows the trapezoidal area resulting for one such nerve fiber cross section vector defined by bases 930 and 932 and height 931.

Given that the area of a trapezoid is its height multiplied by its average base, the effective cross-sectional areas for each nerve fiber cross-section vector, $t_j$, drawn at each point, i, at the set of points, N, around the optic disc margin, can be calculated. The outer base is a section of the perimeter of the optic disc margin so its length is $2\pi r_i/N$ where $r_i$ is the shortest distance from the optic disc margin to the central vector at the point, i. The inner base's length is:

$$\frac{2\pi}{N}(r_i - d_{ij}\cos\theta_{ij})$$

where $d_{i,j}$ is the distance from the optic disc margin to the VRI at a specific point, i, for each nerve fiber vector, $t_j$ and $\theta_{i,j}$ is the angle between the nerve-fiber vector and the plane of the optic disc at point, i for each nerve fiber vector, $t_j$. The area, $a_{i,j}$, at a specific point on the optic disc margin, i, for each nerve fiber vector, $t_j$ is therefore:

$$a_{ij} = d_{ij}\left(\frac{\frac{2\pi r_i}{N} + \frac{2\pi}{N}(r_i - d_{ij}\cos\theta_{ij})}{2}\right)$$

which can be simplified to:

$$a_{i,j} = \frac{\pi}{N}(d_{i,j}(2r_i - d_{i,j}\cos\theta_{i,j}))$$

Figure 10:
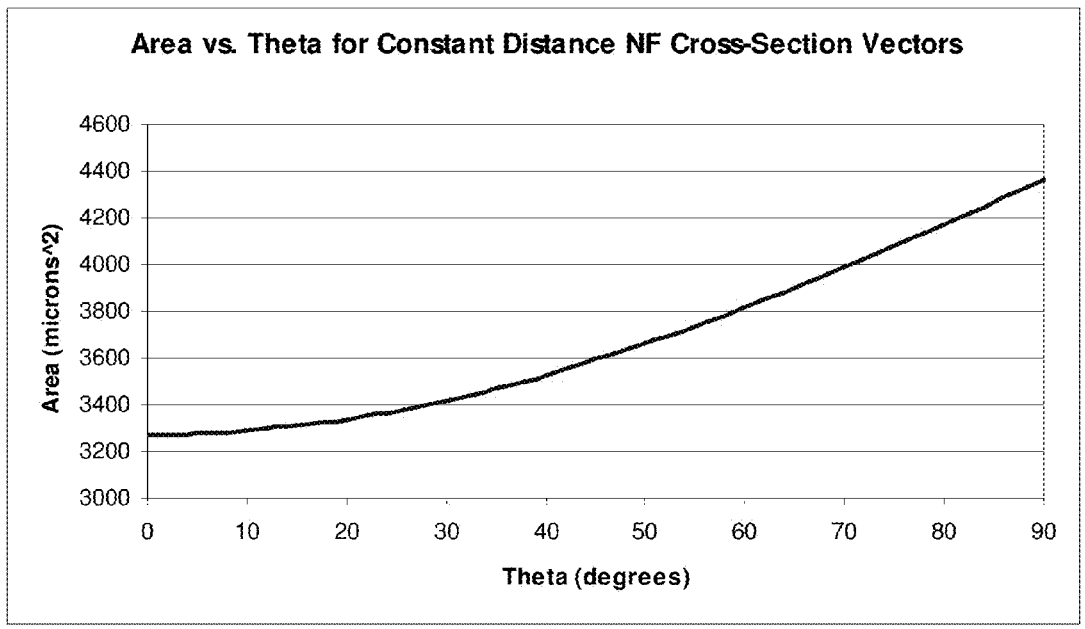
FIG. 10 shows how the areas corresponding to a series of nerve fiber cross section vectors with the same lengths change as a function of the angle, θ, between the nerve fiber cross section vector and the plane of the optic disc.

FIG. 10 illustrates how the area varies with respect to the angle, theta ($\theta_i$), that the nerve fiber cross section vector makes with the plane of the optic disc for a constant distance measurement at a specific point around the optic disc margin, i.e. the case of multiple nerve fiber cross sectional vectors of the same length. The calculations assume that $d_i$=250 microns, $r_i$=500 microns, N=180, meaning that 180 points were sampled around the optic disc margin, i.e. in two degree increments.

Further aspects of the invention include identifying for each point i, in the set of points around the optic disc margin, the nerve cross-section vector that produces the minimum effective cross sectional area at that point on the optic disc margin 505. This minimum effective cross sectional area can be thought of as representing the bunching of the nerve fiber layers as they pass through the hole in the optic disc, leading to an increase in effective cross-sectional area for a given length nerve fiber cross section vector as the angle between the nerve fiber vector and the plane of the optic disc increases from zero.

This set of vectors that define the minimum effective cross sectional areas for all the sampled points around the optic disc margin serve as an important basis to the analysis of the neuroretinal rim that constitute further embodiments of the invention. The nerve fiber or neuroretinal rim area can be calculated (510) by summing the minimum effective cross-sectional areas for all points sampled around the optic disc margin. As mentioned above, this provides an unambiguous, repeatable and clinically meaningful definition of the neuroretinal rim as being defined by the points that minimize the area of nerve fiber exiting the eye through the chorioscleral canal.

As with all digital imaging, the 3D image data is a discretely sampled representation of the tissue being imaged. Care must then be taken to preserve the accuracy of the measurements. A further embodiment of the invention is that, when defining vectors to the VRI to identify the minimum cross-sectional area, interpolation can be used to insure accuracy in the measurement. Despite the discrete intervals afforded by the surface of the VRI in the digitized image volume, it is possible to interpolate between the endpoints of the vectors on the VRI surface. This could be done in a continuous fashion, or as a fast approximation, use simple geometry to estimate the line between the two discrete VRI surface points, and then find the minimum distance to that line (which is perpendicular) and use that to calculate the area measurement at the interpolated location.

A further aspect of the invention is to provide a display or representation of the minimum area determination to the clinician. The basic idea of the representation is to collapse the measurement into a lower dimension (from 3D to 2D). The area of the neuroretinal rim might, for example, be in the form shown in FIG. 9; i.e., the surface area of an irregular conical section. In order to collapse this measure and present it in a 2D image one can calculate what distances would have been measured to yield the same area measurements where the angle they make with the plane of the disc was zero degrees. This is illustrated in FIG. 11*a*. For the purpose of discussion we define the shape generated by the end points of the minimum area vectors as an intermediate cup margin, as we transform these vectors to generate our representation of the actual optic cup margin (often called optic cup). Assuming the intermediate cup margin 1105 and optic disc margin 1104 have been determined using the invented algorithm, the minimum area vectors are then rotated down into the plane of the disc (i.e., make $\theta_i$=0 degrees) and adjusted in length $d_i$ such that the rim area calculated is the same leading to a proposed cup-disc schematic 1103. The optic disc margin is then identified as being the shape defined by the endpoints of these adjusted vectors. This proposed representation communicates accurately the true measurement in a 2D form that emulates that created by a more traditional ophthalmic examination and clinician expertise. Taking the illustration in FIG. 11*a* as an example, that is, if it were an actual cross-section of an optic nerve, using this representation one would say that the nerve fiber bundle is large, and therefore should have a small cup, indicating relatively good health of the ONH. But if one simply projects the intermediate cup margin 1105 onto a 2D plane, the resultant cup-disc schematic 1106 shows significant cupping. Furthermore, this appears to be what a clinician infers when drawing a disc and cup having viewed a patient's fundus photographs or from the slit lamp exam. FIGS. 11*b* and 11*c* show drawings of the projected cup and proposed cup respectively. Having defined both the optic disc margin, and optic cup margin in the 2D plane similar to what a clinician draws, one can derive other parameters commonly used by clinicians, such as cup to disc ratio, being the ratio of the optic cup size to optic disc size, or neuroretinal rim width, being the distance from the optic disc margin to optic cup margin around the disc.

Neuroretinal rim thicknesses and the other derived parameters can be compiled over a range of healthy and diseased eyes to serve as a normative database for comparison either as a global measurement or across various meridians of the 3D image data 511. This area can also be used as the basis of a normative database for comparison. Cup and disc margins can be calculated globally or for specific meridians of a 3D image data set and also serve as measurements for comparison between healthy and diseased eyes. These parameters can be tracked over time to evaluate disease progression and efficacy of treatment.

A preferred embodiment for achieving this projected representation is described in detail below. The neuroretinal rim thickness can be defined for each point on the optic disc margin as the thickness the nerve fiber layer would be at the intersection with the optic disc surface by transforming the vector $t_i$ into a vector in the plane of the optic disc surface, $t_{i'}$ using a mathematical model. One such mathematic model would be to assume that the fiber tissue consists of cylinders of fixed diameters lying in the plane defined by the set of nerve fiber cross section vectors and that the vector $t_i$, extends from the optic disc margin to the VRI. The vector can be transformed into a vector in the plane of the optic disc according to the formula: $d_i' \Rightarrow r_i - \sqrt{r_i^2 - 2r_i d_i + d_i^2 \cos\theta_i}$ as derived below. (Note the subscript j is dropped from the equation, as $d_i$ are the distances that yielded the minimum area for a search over all possible vectors j). To determine the $d_i$ where $\theta i=0$ degrees, one must solve for the roots of a quadratic equation:

$$-d_i^2 \cos\sigma + 2r_i d_i \cos\theta - a_i N/\pi = 0,$$

given that Cos(0) is one. The solution is of the form:

$$\Rightarrow d_i^2 - 2r_i d_i + a_i N/\pi = 0$$

$$\frac{-B \pm \sqrt{B^2 - 4AC}}{2A},$$

where $A=1$, $B=-2r_i$, and $C=a_i$. Therefore $$d_i' = \frac{2r_i \pm \sqrt{4r_i^2 - 4a_i \frac{N}{\pi}}}{2}, \Rightarrow d_i' = \frac{2r_i - \sqrt{4r_i^2 - 4a_i \frac{N}{\pi}}}{2} \Rightarrow d_i' =$$

$$r_i - \sqrt{r_i^2 - a_i \frac{N}{\pi}} \Rightarrow r_i - \sqrt{r_i^2 - 2r_i d_i + d_i^2 \cos\theta_i}$$

Only the negative root is selected because the positive root would result in solutions with a distance longer than the distance to the central vector, producing an anatomically meaningless result.

Figure 12A:
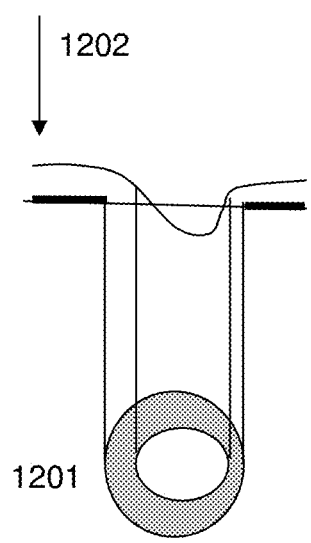
FIGS. 12a, 12b and 12c illustrate the advantage of the invention in the case of variations in viewing angle.
Figure 12B:
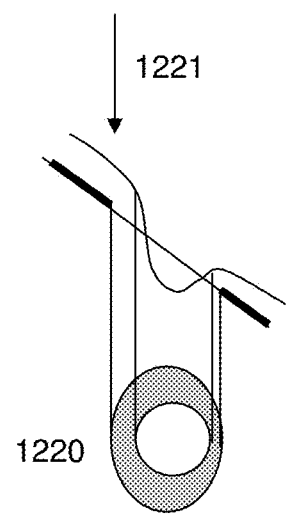
Figure 12C:
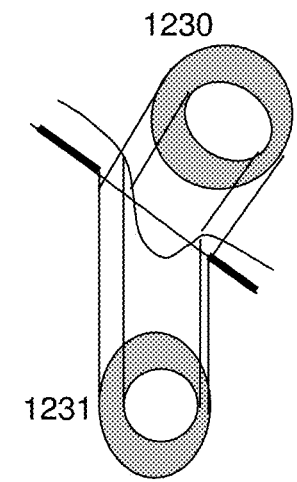

As FIGS. 12a, 12b, and 12c show, one effect that this has is to render a 2D representation of the ONH architecture and corresponding cup and disc areas as if the ophthalmologist is looking along the axis of the ONH itself, perpendicular to the optic disc plane; i.e., not restricted to the viewing angle available to the clinician, through the pupil of the eye. This is advantageous for any tilted ONH. FIG. 12a illustrates the representation 1201 when the disc is perpendicular to the viewing angle where the viewing angle is indicated by arrow 1202. In this case the derived rim, cup and disc areas are the same as the areas in the displayed image as seen by the clinician. If the same disc is viewed from a different angle as illustrated in FIG. 12b, that is not perpendicular to the plane of the optic disc (arrow 1221), the projected cup and disc 1220 seen by the clinician is foreshortened, leading to the drawing of a foreshortened image by the clinician, and therefore smaller cup and disc areas. The analysis methods described as part of the invented method will preserve the true values as if the ophthalmologist is looking along the axis of the ONH itself as shown in representation 1230 compared to representation 1231 seem in FIG. 12c. For the purpose of display, one may wish to show the optic disc and cup margins viewed along the OCT imaging axis, rather than viewing along the axis of the ONH itself, as this is the view seen by the clinician, and the view created by integrating the OCT A-scans to generate an en-face OCT image. If the OCT imaging axis is not along the ONH axis, viewing along the OCT axis foreshortens the cup and disc images somewhat, but allows it to be superimposed on the OCT en-face image. Although the images are foreshortened, one would not change the calculated areas for neuroretinal rim, optic cup, and optic disc.

A further aspect of the invention is to improve the analysis to account for abnormalities in the nerve fibers that could lead to representations that are inconsistent with anatomy or the analysis a clinician would provide. Exclusion criteria can be applied to the set of cross-section vectors to account for these abnormalities, reducing the subset of vectors considered in the algorithm and obtaining a more accurate measurement. Reasons for exclusion could include having too large of an angle relative to the optic disc or could be based on the slope or edge of the VRI in the plane defined by the set of vectors. Additional exclusion criteria could include excluding portions of the VRI as endpoints for the surface based on the topography of the VRI.

FIGS. 13a-d show various aspects of the output that could be provided using the invented method. FIG. 13a shows the cup 1301 and disc 1302 margins drawn for one eye of a patient. The area between the two is the neuroretinal rim and the representation preserves the depth information obtained from the analysis on the 3D OCT image data, a cross-section of which is shown in FIG. 13b. The small circles in FIG. 13b correspond to the locations of the optic cup margin 1301. It is should be noted that although we calculate the areas of the cup and disc in the plane of the optic disc, the preferred embodiment on cross sectional images such as FIG. 13b is to show the optic cup margins as being on the VRI boundary by projecting them up from the optic disc surface to the VRI either along the OCT axis, or along the ONH axis (perpendicular to the optic disc plane.) If the optic cup margin is projected up to the VRI boundary in this manner, a 3D cup volume can be defined between the VRI and a surface fitted across the points in the projected optic cup margin that can be reported and used for comparison via a normative database.

FIG. 13c displays the neuroretinal rim thickness as a function of angle around the optic disc margin for both the left and right eyes. FIG. 13d shows a table of parameters calculated from the analysis including the rim area, cup to disc ration and cup volume. A further aspect of the invention includes comparing outputs of the analysis such as the neuroretinal rim thickness or area to a normative database for the purposes of disease diagnosis and tracking.

Although the illustrated embodiments are limited to SD-OCT data, the analysis methods described herein may be used with other types of 3D image data obtained through other modalities. The method is intended to be carried out automatically via a processor attached to an imaging system but could be performed manually as well. The analysis can be carried out during data collection or could be stored and recalled for subsequent analysis. Data from various stages of the analysis and representation could be stored and recalled at a later point in time for comparison. Furthermore, the present invention does not need to follow the exact sequence as shown in FIG. 5, as other additional steps can be inserted to perform substantially equivalent operations. Although various embodiments that incorporate the teachings of the present invention have been shown and described in detail herein, those skilled in the art can readily devise many other varied embodiments that still incorporate these teachings.

The following references are hereby incorporated by reference.

U.S. PATENT DOCUMENTS

U.S. Pat. No. 6,415,173, Sponsel et al., "Method for Analyzing the Optic Nerve Disc from Stereo Color Photographs using Vascular Landmarks"

U.S. Pat. No. 6,698,885, Berger et al., "Judging Eye Changes in Images of the Eye"

U.S. Pat. No. 7,203,351, Swindale et al., "Analysis of Optic Nerve Head Shape"

U.S. Pat. No. 7,712,898, Abramoff et al., "Methods and Systems for Optic Nerve Head Segmentation"

OTHER PUBLICATIONS

Anderson, D. (2004) "The Optic Nerve Head in Glaucoma" Duane's Ophthalmology.

Frohman E et al. (2008). "Optical Coherence Tomography: A Window into the mechanisms of multiple sclerosis" *Nat. Clin. Prac. Neurol.* 4(12): 664-675.

Coleman A. et al. (1996). "Interobserver and intraobserver variability in the detection of glaucomatous progression of the optic disc" *J. Glaucoma* 5:384-9.

Tielsch J. et al. (1988) "Intraobserver and interobserver agreement in measurement of optic disc characteristics" *Ophthalmology* 95:350-6.

Heidelberg on-line FAQ: http://www.heidelbergengineering-.com/technical-support-heidelberg-engineering/faq-topics/hrt3-glaucoma-faqs/#faq_791.

Poli A. et al. (2008). "Analysis of HRT images: comparison of reference planes" *Ophthalmology & Visual Science* 49(9)).

Savini G et al. (2009). "Agreement between optical coherence tomography and digital stereophotography in vertical cup-to-disc ratio measurement" *Graefe's Arch. Clin. Exp. Ophthalmol* 247(3):377-383.

Leung C. et al (2005). "Analysis of Retinal nerve fiber layer and optic nerve head in glaucoma with different reference plane offsets using optical coherence tomography" *Invest Ophthalmol and Vis Sci* 46:891-899.

Radius R. et al. (1979). "The course of axons through the retina and optic nerve head" *Arch Ophthalmol* 97(6):1154-8.

Minckler D. (1980). "The organization of nerve fiber bundles in the primate optic nerve head" *Arch Ophthalmol* 98(9): 1630-6.

Choma, M. A. et al. (2003). "Sensitivity advantage of swept source and Fourier domain optical coherence tomography." *Optics Express* 11(18): 2183-2189.

Chen T. (2009). "Spectral domain optical coherence tomography in glaucoma: Qualitative and quantitative analysis of the optic nerve head and retinal nerve fiber layer (an AOS thesis)" *Trans Am Ophthalmol Soc* 107:254-281.

Knighton R. et al (2006) "The Structure of the optic nerve head as assessed by spectral domain optical coherence tomography" ARVO poster presentation.

Medeiros F. et al (2009). "Detection of glaucoma progression with Stratus OCT retinal nerve fiber layer, optic nerve head, and macular thickness measurements" *Investigative Ophthalmology and Visual Science* 50:5741-5748.

Povazay B. et al. (2007). "Minimum distance mapping using three-dimensional optical coherence tomography for glaucoma diagnosis" *J. Biomed. Opt.* 12:041204).

Morgan J. (2004) "Circulation and axonal transport in the optic nerve" *Eye* 18:1089-1095.

What is claimed is:

1. A method of evaluating the neuroretinal rim of a patient, said method comprising the steps of:
   acquiring a 3D volume of intensity data using an optical coherence tomography (OCT) device, said volume including the optic nerve head;
   identifying the vitreoretinal interface (VRI) from the 3D data;
   defining an optic disc margin from the 3D data;
   determining a value corresponding to the minimum area of a 3D surface between the optic disc margin and the VRI; and
   displaying the value;
   wherein said step of determining a value corresponding to the minimum area of a 3D surface between the optic disc margin and the VRI comprises the steps of:
   dividing the optic disc margin into sectors;
   determining a value corresponding to the minimum area of a surface from the optic disc margin to the VRI for each sector; and
   summing the determined values.

2. A method as recited in claim 1, wherein the method is automated.

3. A method as recited in claim 1, wherein the optic disc margin is defined in reference to the endpoints of Bruch's membrane.

4. A method as recited in claim 1, wherein the optic disc margin is defined by interpolation when there is uncertainty in the identification of the disc margin.

5. A method as recited in claim 1, wherein the optic disc margin is defined in reference to the endpoints of the support structure of the retinal pigment epithelial RPE.

6. A method as recited in claim 1, further comprising comparing the determined value to a normative database of areas.

7. A method of evaluating the neuroretinal rim of a patient, said method comprising the steps of:
   acquiring a 3D volume of intensity data using an optical coherence tomography (OCT) device, said volume including the optic nerve head;
   identifying the vitreoretinal interface (VRI) from the 3D data;
   defining an optic disc margin from the 3D data;
   determining a value corresponding to the minimum area of a 3D surface between the optic disc margin and the VRI, wherein the determination is improved by limiting the angle of the surface relative to the optic disc; and
   displaying the value.

8. A method as recited in claim 1, wherein the step of determining the value includes excluding portions of the VRI as endpoints for the surface based on the topography of the VRI.

9. A method of evaluating the neuroretinal rim of a patient, said method comprising the steps of:
   acquiring a 3D volume of intensity data, said volume including the optic nerve head using an optical coherence tomography (OCT) device;
   identifying the vitreoretinal interface (VRI) from the 3D data;
   defining an optic disc margin from the 3D data;
   determining the minimum area of a 3D surface between the optic disc margin and the VRI; and
   displaying an image that identifies the determined area in a 2D format;
   wherein said step of determining the minimum area of a 3D surface between the optic disc margin and the VRI comprises the steps of:
   dividing the optic disc margin into sectors and determining the minimum area of a surface from the optic disc margin to the VRI for each sector.

10. A method as recited in claim 9, wherein the method is automated.

11. A method as recited in claim 9, wherein the optic disc margin is defined in reference to the endpoints of Bruch's membrane.

12. A method as recited in claim 9, wherein the optic disc margin is defined by interpolation when there is uncertainty in the identification of the optic disc margin.

13. A method as recited in claim 9, wherein the optic disc margin is defined in reference to the endpoints of the support structure of the retinal pigment epithelial (RPE).

14. A method as recited in claim 9, wherein the outer border of the determined area is the optic disc margin.

15. A method as recited in claim 9, wherein the inner border of the determined area is defined as the optic cup margin.

16. A method as recited in claim 9, wherein the displayed image involves showing the neuroretinal rim as the region between the optic disc margin and the optic cup margin.

17. A method as recited in claim 9, wherein the displayed image is a 2D representation of the determined area that imitates what would be seen if looking along the axis of the optic nerve head (ONH).

18. A method as recited in claim 9, wherein the displayed image is a 2D representation of the determined area that imitates what would be seen if looking along the axis along which the OCT data was collected.

19. A method as recited in claim 9, further comprising defining an optic cup margin as a shape whose area is based on the difference in the area of the optic disc and the minimum area surface from the optic disc margin to the VRI and displaying the optic cup margin.

20. A method as recited in claim 19, further comprising defining the optic cup margin shape in the plane of the optic disc.

21. A method as recited in claim 20, further comprising projecting the optic cup margin shape from the plane of the optic disc up to the VRI surface.

22. A method as recited in claim 21, further comprising defining a cup volume as the volume between the VRI and a surface fitted across the points in the projected optic cup margin.

23. A method as recited in claim 19, wherein the area is the difference in the area of the optic disc and the value corresponding to the minimum area of a surface from the optic disc margin to the VRI.

24. A method as recited in claim 9, further comprising defining an optic cup margin as a shape in the plane of the optic disc wherein the area of each of its sectors is based on the difference in the area of the sector of the optic disc and the minimum area from the optic disc margin to the VRI for the sector.

25. A method as described in claim 9, wherein the area of each of its sectors is the difference in the area of the sector of the optic disc and the minimum area from the optic disc margin to the VRI for the sector.

26. A method of performing structural analysis on a neuroretinal rim of a patient comprising:
acquiring a 3D volume of intensity data, said volume including the optic nerve head using an optical coherence tomography (OCT) device;
identifying the vitreoretinal interface (VRI) from the 3D data;
defining an optic disc margin from the 3D data;
defining a series of vectors extending from points around the optic disc margin and extending to the VRI and pointing towards a centrally located axis that runs perpendicular through the optic disc margin; and
calculating a minimum cross-sectional area for regions associated with each of the vectors, where these cross-sectional areas are a function of at least the distance from the axis to the point on the disc margin, the angle between the VRI and the plane of the optic disc for each vector, and the length of the vector; and
generating an output based on the area calculations as a diagnostic of ocular health.

27. A method as recited in claim 26, wherein the optic disc margin is defined in reference to the endpoints of Bruch's membrane.

28. A method as recited in claim 26, wherein the optic disc margin is defined by interpolation when there is uncertainty in the identification of the optic disc margin.

29. A method as recited in claim 26, wherein the cross-sectional areas for each nerve fiber cross-section vector, $t_j$, drawn at each point, i, at the set of points, N, around the optic disc margin, are calculated according to:

$$a_{i,j} = \frac{\pi}{N}(d_{i,j}(2r_i - d_{i,j}\cos\theta_{i,j}))$$

where $a_{i,j}$ is the area at a specific point on the optic disc margin, i, for each nerve fiber vector, $t_j$;
$d_{i,j}$ is the distance from the optic disc margin to the VRI at a specific point, i, for each nerve fiber vector, $t_j$;
$r_i$ is the shortest distance from the optic disc margin to the central vector in the plane of the optic disc at the point, i; and
$\theta_{i,j}$ is the angle between the nerve-fiber vector and the plane of the optic disc at point, i for each nerve fiber vector, $t_j$.

30. A method as recited in claim 29, further comprising identifying for each point, i, in the set of points around the optic disc margin, a nerve cross-section vector, $t_i$, that produces the minimum cross-sectional area at that point.

31. A method as recited in claim 30, wherein the vector that produces the minimum cross-sectional area at a point on the optic disc margin is selected from a subset of the vectors based on additional exclusion criteria.

32. A method as recited in claim 31, wherein the additional exclusion criteria includes excluding vectors having an angle relative to the optic disc that exceeds a predetermined maximum value.

33. A method as recited in claim 31, wherein the additional exclusion criteria includes excluding vectors based on the slope or edge of the VRI in the plane defined by the set of vectors.

34. A method as recited in claim 30, further comprising defining the optic cup margin as the shape enclosed by the endpoints of vectors generated by transforming each vector t, into the plane of the optic disc surface through a mathematical model.

35. A method as recited in claim 34, further comprising determining a cup to disc ratio.

36. A method as recited in claim 30, further comprising displaying at least one representation of the analysis.

37. A method as recited in claim 30, further comprising defining a neuroretinal rim thickness for each point on the optic disc margin as the thickness the nerve fiber layer would be at the intersection with the optic disc surface, where the vector t, is transformed into a vector in the plane of the optic disc surface through a mathematical model.

38. A method as recited in claim 37, further comprising comparing the neuroretinal rim thicknesses to a normative database.

39. A method as recited in claim 37, where the vector is transformed into a vector in the plane of the optic disc surface of length $d_i'$ following the following formula $$d_i' \Rightarrow r_i - \sqrt{r_i^2 - 2r_i d_i + d_i^2 \cos\theta_i}.$$

40. A method as recited in claim 39, further comprising displaying the length of the vectors versus azimuthal angle for points around the optic disc margin.

41. An optical coherence tomography (OCT) system, the OCT system including a light source generating a light beam, a sample arm, a reference arm and a detection arm, said OCT system comprising:
- a scanner for scanning the light beam to a plurality of positions in an X/Y plane;
- a detector coupled to the detection arm for generating output signals in response to light collected from the sample arm and the reference arm, said output signals corresponding to a reflectance intensity distribution as a function of depth:
- a processor for controlling the scanning optics and for receiving the output signals generated by the detector, said processor operating to acquire a 3D volume of intensity data, said volume including the optic nerve head, said processor identifying the vitreoretinal interface (VRI) from the 3D data and defining an optic disc margin from the 3D data, said processor determining a value corresponding to the minimum area of a 3D surface between the optic disc margin and the VRI; and
- a display for displaying the value wherein said the processor determines the value corresponding to the minimum area of a 3D surface between the optic disc margin and the VRI by dividing the optic disc margin into sectors, determining a value corresponding to the minimum area of a surface from the optic disc margin to the VRI for each sector and summing the determined values.

42. An apparatus as recited in claim 41, wherein the optic disc margin is defined in reference to the endpoints of Bruch's membrane.

43. An apparatus as recited in claim 41, wherein the optic disc margin is defined by interpolation when there is uncertainty in the identification of the disc margin.

44. An apparatus as recited in claim 41, wherein the optic disc margin is defined in reference to the endpoints of the support structure of the retinal pigment epithelial RPE.

45. An optical coherence tomography (OCT) system, the OCT system including a light source generating a light beam, a sample arm, a reference arm and a detection arm, said OCT system comprising:
- a scanner for scanning the light beam to a plurality of positions in an X/Y plane;
- a detector coupled to the detection arm for generating output signals in response to light collected from the sample arm and the reference arm, said output signals corresponding to a reflectance intensity distribution as a function of depth:
- a processor for controlling the scanning optics and for receiving the output signals generated by the detector, said processor operating to acquire a 3D volume of intensity data, said volume including the optic nerve head, said processor identifying the vitreoretinal interface (VRI) from the 3D data and defining an optic disc margin from the 3D data, said processor determining the minimum area of a 3D surface between the optic disc margin and the VRI; and
- a display for displaying an image that identifies the determined area in a 2D format wherein said the processor determines the minimum area of a 3D surface between the optic disc margin and the VRI by dividing the optic disc margin into sectors and determining the minimum area of a surface from the optic disc margin to the VRI for each sector.

46. An apparatus as recited in claim 45, wherein the optic disc margin is defined in reference to the endpoints of Bruch's membrane.

47. An apparatus as recited in claim 45, wherein the optic disc margin is defined by interpolation when there is uncertainty in the identification of the disc margin.

48. An apparatus as recited in claim 45, wherein the optic disc margin is defined in reference to the endpoints of the support structure of the retinal pigment epithelial RPE.

49. An apparatus as recited in claim 45, wherein the displayed image is a 2D representation of the determined area that imitates what would be seen if looking along the axis of the optic nerve head ONH.

50. An apparatus as recited in claim 45, wherein the displayed image is a 2D representation of the determined area that imitates what would be seen if looking along the axis along which the OCT data was collected.

51. A method as recited in claim 26, wherein the axis runs through the center of the optic disc margin.

52. A method as recited in claim 26, wherein the axis is perpendicular to the surface of the optic disc margin.

* * * * *